United States Patent [19]

Wagner

[11] Patent Number: 5,352,416

[45] Date of Patent: Oct. 4, 1994

[54] VALVE ARRANGEMENT FOR A STERILIZATION CONTAINER

[75] Inventor: Peter Wagner, Söcking/Kr. Starnberg, Fed. Rep. of Germany

[73] Assignee: Wagner GmbH, Munich, Fed. Rep. of Germany

[21] Appl. No.: 862,808

[22] Filed: Apr. 3, 1992

[30] Foreign Application Priority Data

| Apr. 5, 1991 [DE] | Fed. Rep. of Germany | 4111075 |
| Apr. 5, 1991 [DE] | Fed. Rep. of Germany | 4111076 |
| Apr. 5, 1991 [DE] | Fed. Rep. of Germany | 4111077 |

[51] Int. Cl.$^5$ ............................................. G05D 16/06
[52] U.S. Cl. .................................. 422/108; 236/48 R; 422/103; 422/114; 422/295
[58] Field of Search ............... 422/108, 111, 114, 103, 422/295; 236/48 R, 101 E

[56] References Cited

U.S. PATENT DOCUMENTS

| 3,980,131 | 9/1976 | Perle et al. | 165/61 |
| 4,303,195 | 12/1981 | Hashimoto et al. | 236/48 R |
| 4,386,732 | 6/1983 | Satomoto | 236/48 R |
| 4,580,719 | 4/1986 | Long, Jr. | 236/34.5 |
| 4,687,635 | 8/1987 | Kaehler et al. | 422/26 |
| 4,948,566 | 8/1990 | Gabele et al. | 422/107 |
| 5,110,559 | 5/1992 | Kondo et al. | 422/109 |

FOREIGN PATENT DOCUMENTS

3202430  7/1983  Fed. Rep. of Germany .

*Primary Examiner*—Robert J. Warden
*Assistant Examiner*—Krisanne M. Thornton
*Attorney, Agent, or Firm*—Ostrolenk, Faber, Gerb & Soffen

[57] ABSTRACT

The valve arrangement for a sterilization container having a pressure chamber with vent openings, includes two valve bodies arranged in the pressure chamber above the vent openings. The valve bodies are controlled by temperature sensors. The temperature sensors employ snap-discs which are disposed above each other in the valve bodies. The temperature sensors of each valve are adjusted to different upper and lower snap temperatures. At least one of the vent openings remains open, with both of the valves closing the vent openings only at a predetermined point during the venting phase of sterilization. A condensation discharge valve can be disposed at an outlet in the lowest point of the bottom of the container. The discharge valve includes a valve body which opens and closes the outlet. The valve body is normally in the open position and is controlled by a temperature sensor also in the form of a snap-disc. The container can include a condensate collection container disposed on the bottom thereof. The condensate collection container has a funnel-shaped top on which a perforated instrument dish can be placed. A condensate inlet valve is arranged at the lowest point on the side of the collection container.

12 Claims, 5 Drawing Sheets

VALVE ARRANGEMENT FOR A STERILIZATION CONTAINER

BACKGROUND OF THE INVENTION

1. Field of the Invention

The present invention relates to a valve arrangement for sterilizer containers, more particularly, to a valve arrangement for a sterilization container which operates without the need for manual action, and while being of simple and cost-favorable construction, assures the desired valve function, not only at a single sterilization temperature, but at different temperatures, and closes only at a predetermined point during the venting phase.

2. Description of the Prior Art

Snap discs are preferably employed as temperature sensors. These snap discs consist of a thermobimetal material and are sold under the trademark "CLICK-FLEX". They are characterized by the fact that at a predetermined temperature, they snap into their opposite state of curvature, and upon cooling through a hysteresis, snap back at a low switch temperature. The snap discs have proven particularly suitable since they can be adjusted very precisely during manufacture to an upper snap temperature and a lower snap temperature and have the advantage that they can switch very rapidly and with a relatively large stroke, which can be further increased by the connection of several discs in series. Another advantage of snap discs is that the structural height of the valve arrangement can be kept very low and the entire construction thereby becomes simple and cheap.

SUMMARY OF THE INVENTION

The valve arrangement for a sterilization container of the present invention comprises two valves arranged in a pressure chamber of the container above vent openings in the chamber. The valve bodies are controlled by temperature sensors. The temperature sensors employ snap-discs which are disposed in the valves. The snap-discs are adjusted to have different upper and lower snap temperatures.

These snap-discs, at least two different types of which are provided, namely one type for each valve, act via valve bodies directly on the vent openings of a pressure capsule in the manner that the openings permit pressure equalization of the capsule to the continuously varying surrounding pressure, during each phase of the sterilization cycle, until the valves then shut the pressure capsules off at a predetermined time during the vacuum-drying phase and thus make it sensitive to subsequent pressure increases.

Accordingly, the pressure increase for the venting of the sterilizer to normal pressure at the end of the sterilization cycle can squeeze these pressure capsules together axially and thus close the fluid exchange openings of the container controlled by the capsules, even before the end of the venting, the remaining increase in pressure no longer taking place within the container and the latter therefore being sealed off by the outside pressure, while maintaining a vacuum therein. For opening, the container must be relieved of pressure by means of, for example, an auxiliary valve.

In accordance with a preferred embodiment of the invention, the valve body is covered by the container lid, which is held open by the pressure capsule, which is designed to collapse during the venting phase, via the valve control, so that the lid remains tightly sealed by the enclosed vacuum or the outer pressure after such closing. In this case, the pressure capsule can be arranged between the container lid and an intermediate lid resting within the container on a lower part thereof, its vent openings leading to the inside of the container.

Another possibility is the use of a fluid exchange valve which is inserted in the lid as an integrated control. In this case, the pressure capsule acts as the support for a valve cap which subsequently closes the fluid exchange holes. The valve cap can be fastened detachably, for instance, by a thread, at a specified distance from the container lid, prior to sterilization, to thus hold the fluid exchange openings open. At the point described, the capsule is squeezed together and the valve cap is thereby pulled tighter and tighter against the lid, until the cap finally closes the fluid exchange openings and seals the container.

In accordance with a further embodiment of the invention, the valve arrangement is arranged in a release device which cooperates with the sterilizer container, but remains structurally separate therefrom. This release device can be placed in succession on as many different sterilization containers as desired so that they can be sealed during sterilization, it being possible after removal from the sterilizer for the release device to be taken off without loss of the seal and used for the next container. By moving the valve control to the outside of the container, which is achieved in this manner, it is no longer necessary to leave the expensive valve control unused during the storage of the containers (up to 6 weeks), and such a system is accordingly cheaper, simpler and easier.

In accordance with a further feature, such a release device is developed as a lid superstructure which has a valve arrangement in accordance with the invention. In this way, the fluid exchange holes of the container are closed at the time already described, via one or more valve caps arranged in the container lid, which are normally held open by spring force. It can be appreciated that during the manufacture the containers can be stacked with the release device placed thereon.

In accordance with a further feature, a release device, also developed as a lid superstructure, closes the container lid acting as a valve cap via a lever system in the form of a rod. Prior to sterilization, the lid lies on axially displaceable spacers arranged in the body of the container at a defined distance from the body, the slot thereby defined between the lid and body forming the fluid exchange opening, and the "release lid" is simply placed on the container prior to sterilization, it being unimportant if additional containers are stacked thereon. At the time described, the release device pushes the spacers axially inward and the lid, supported by the prestressing force of the closure, closes the container. In this case, the container and lid no longer require any auxiliary valves and can therefore be produced simply and at low cost.

The invention also refers to a condensate discharge valve which provides assurance that complete drying is always effected, regardless of the mass of the instruments to be sterilized.

In this connection, the invention also has the further object of providing a condensate discharge valve which permits the condensate to be discharged reliably, and closes in a continuously gas-tight manner after the closing of the vacuum valve.

The condensate discharge valve includes a temperature sensor which opens the valve at a first predetermined temperature. The valve remains open until the temperature sensor switches the valve to a closed position during a drying phase when the temperature of the sensor reaches a second predetermined temperature, below the first predetermined temperature. The temperature sensor is formed by a snap-disc arrangement. A precisely defined temperature control with relatively high control pressure can be obtained by the snap-disc arrangement.

Another object of the invention is to permit the removal of the condensate from the materials sterilized, and thus the dependable drying thereof, without requiring a special valve in the sterilization container for this purpose.

A condensate collection container is installed on the bottom of the container. The condensate collection container includes a condensate inlet valve which remains open during steam sterilization. After sterilization the valve is closed to seal the collection container to prevent condensate from collecting therein.

Since the collection container is a flat, closed and mobile container, it can be used within any sterilization container or package, and therefore different sterilization containers, even by different manufacturers, as well as soft packings such as sterilization paper or bags can accommodate the collection container. In cases when only drying problems arise, an economic advantage is also gained, since such a device, which can be purchased individually at any time, may be used only when required.

BRIEF DESCRIPTION OF THE DRAWINGS

Several embodiments of the invention will be described below with reference to the drawings, in which.

DETAILED DESCRIPTION OF THE PREFERRED EMBODIMENTS

Figure 1:
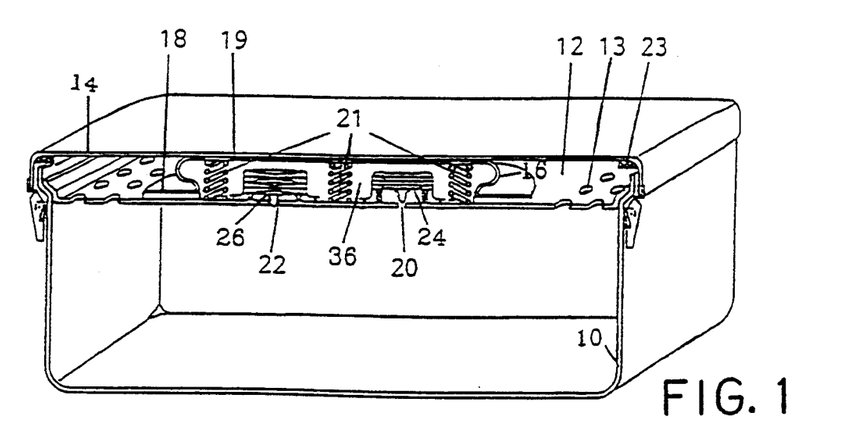
FIG. 1 is a perspective view of a sterilization container developed in accordance with the invention, having a valve arrangement with snap-discs arranged in the lid.
Figure 6:
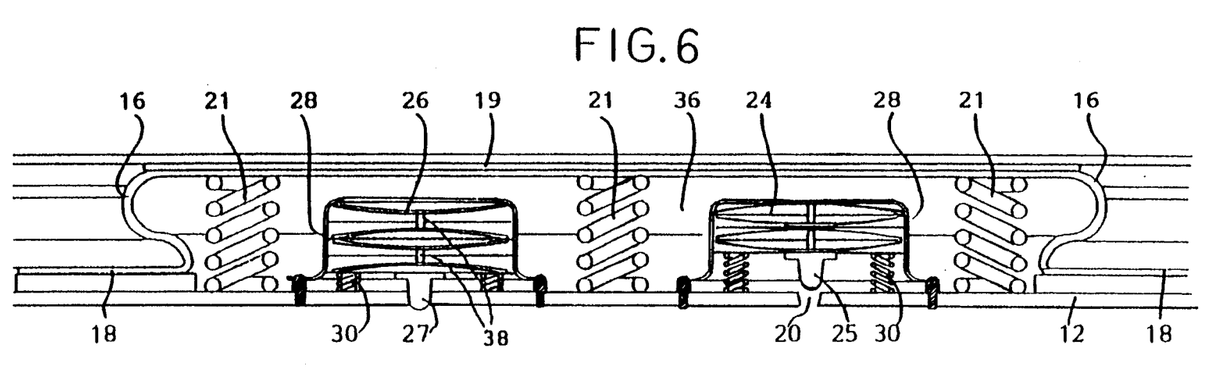
FIG. 6 shows, on a larger scale, a cross-sectional view of the valve arrangement of FIG. 1.

FIG. 1 shows a sterilization container in which the lid is developed as a valve cap. FIG. 6 shows the valve arrangement used in this container on a larger scale.

The sterilization container has a container lower part 10, an intermediate lid 12 and a container lid 14 acting as the valve cap. The intermediate lid 12 rests on an outwardly directed step adjacent the sealing edge of the lower part and has pressure equalization openings 13 through which the exchange of fluid can take place during the sterilization process within the sterilizer.

An elastic bellows 16 is fastened in a sealed manner on the intermediate lid 12 by means of an annular flange 18. Furthermore, as shown in FIG. 6, the bellows 16 rests via a plate 18 against the inside of the container lid 14. Three compressed coil springs 21 are arranged at equal distances spaced around the center of the bellows and are attached between the intermediate lid 12 and the plate 19 to hold the lid seal 23 at a predetermined distance from the sealing edge of the container lower part 10, in the condition of rest with the lid closed. The container closures are developed elastically so that they permit this spacing and thus urge the lid into the closed position.

Within the part of the intermediate lid 12 which is enclosed by the bellows 16, there are two vent holes 20 and 22. The pressure equalization openings 13 are not present in the part of the intermediate lid which is surrounded by the bellows 16.

Valve bodies 25 and 27 are supported by snap-discs or snap-disc packages 24 and 26 and cooperate with the vent holes 20 and 22, respectively. These snap-discs 24 and 26 are surrounded by caps 28 and the lower flange of which is riveted to the intermediate lid 12. The compression coil springs 30 urge the snap-discs upward against the caps 28.

The bellows 16, together with the part of the intermediate lid 12 surrounded by it, form a chamber 36 which is sealed off on all sides and pressure equalization of which can take place only via the vent holes 20 and 22.

Figure 9:
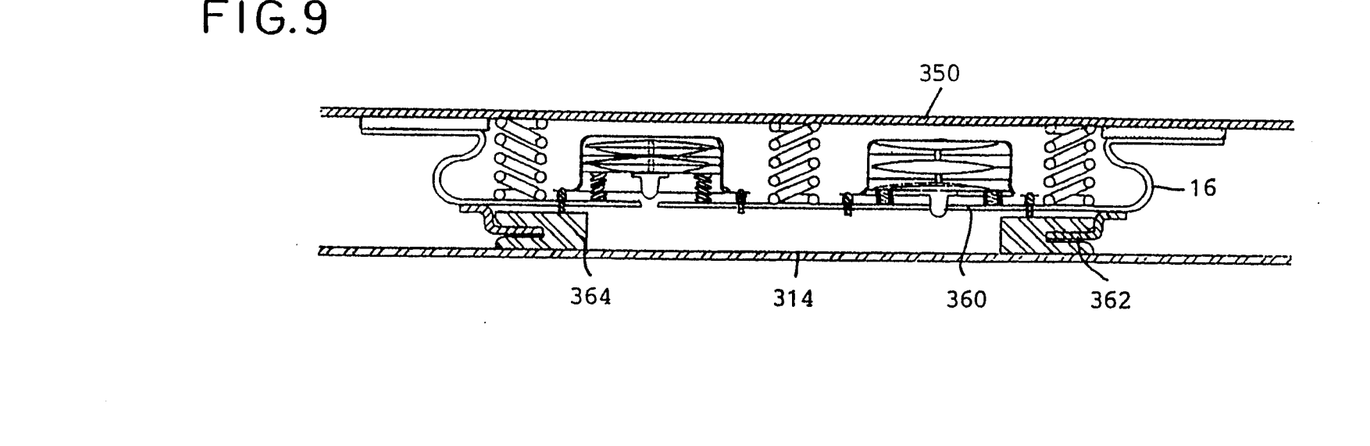
FIG. 9 shows, on a larger scale, the lid-valve arrangement of FIG. 7.

The snap-discs 24, 26 consist of a thermobimetal material and switch over into their opposite state of curvature at a predetermined temperature. Upon cooling, they snap back through hysteresis at a lower temperature. The snap-discs 24 and 26 are so installed that the vent hole 22 is closed at room temperature (FIG. 9).

The snap-discs 24 in their basic position at, for instance, room temperature, together with the centrally arranged spacer rivets 38 thereof, form a package which is not further compressible by the springs 30. In this condition, the valve body 25 is held open by the springs 30 at a defined distance from the vent hole 20. The spacer rivets 38 correspond in their height to the height of curvature between the two discs whose concave sides face each other.

Figure 2:
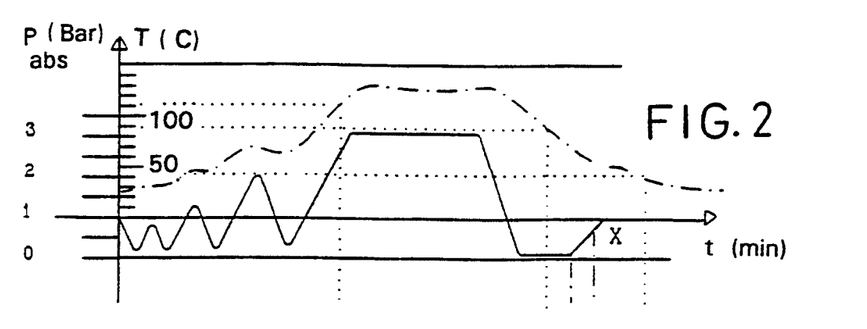
FIG. 2 is a graph which shows the variation of pressure and temperature in the sterilizer as a function of time.
Figure 3:
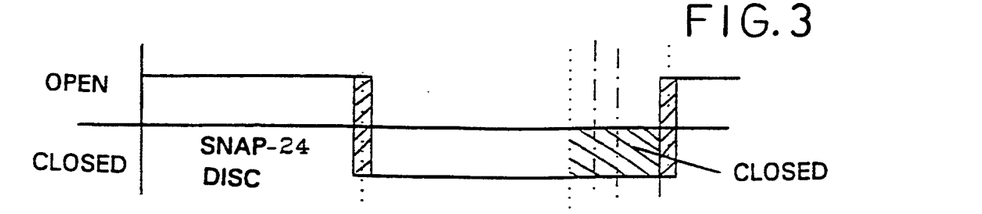
FIGS. 3 to 5 are graphs which show the state of switching of the individual valves during the period of time in accordance with FIG. 2.
Figure 4:
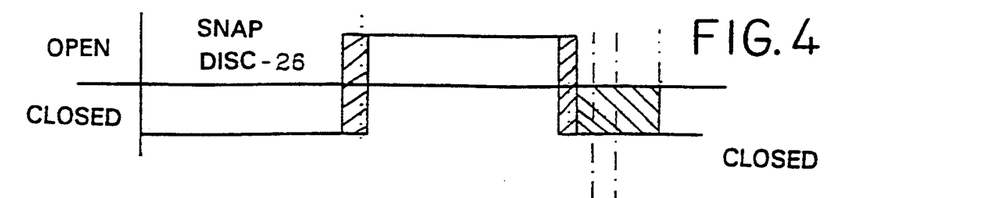
Figure 5:
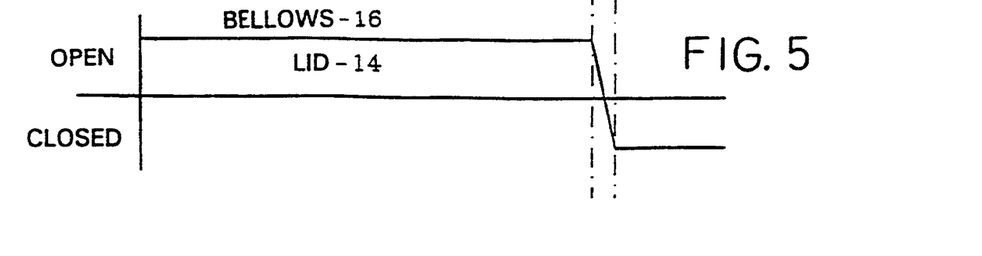

FIG. 2 shows the variation with time of the pressure and temperature during a sterilization process within the sterilizer. The dash-dot line shows the variation of the temperature and the solid line the variation of the pressure. In accordance with the embodiment shown, the snap-discs 24 and 26 are so developed that they switch at the start of the sterilization phase at a temperature of, for instance, 115° C. The pressure equalization takes place via the vent hole 22, with the hole 20 being closed. The snap-discs snap back into the original state through hysteresis upon a reduction in temperature. This switching back takes place at different temperatures of, for instance, 90° C. for snap-disc 26 and 50° C. for snap-disc 24. The temperature of 90° is obtained in the drying phase. As a result, the hole 22 is again closed and the chamber 36 is closed off under vacuum so that no further pressure equalization can take place. In this way, during the venting phase, the lid 14 which has been kept open until now is closed at the time X, since the chamber 36 is pressure-sensitive at this time and, upon increase in pressure, is squeezed axially together in a defined fashion against the springs 21 until, at a predetermined time, the seal of the lid contacts the edge of the container so that upon further external increase in pressure within the sterilization container no further entry of air or steam into the container is possible. A vacuum remains after shutting-off of the venting, the vacuum sealing off the container. The time X can be freely determined within wide ranges, via the effective cross-section of the chamber 36 and the spring rate of the springs 21. The valve function in this connection is as follows:

Up to the switch point of 115° C., both snap-discs 24, 26 remain in the position shown in FIGS. 1 and 6, the venting taking place through the hole 20. At 115° C., both snap-discs snap over. Vent hole 20 is closed and vent hole 22 is opened, so that a pressure equalization can continue to take place and the lid 14 remains raised as a result of which the exchange of fluid in the sterilizer can continue. When the temperature in the drying phase has dropped to, for instance, 90° C., the snap-disc 26 snaps and closes the vent hole 22. Both vent holes 20 and 22 now remain closed, since the snap-disc 24 has a lower switch-back temperature, for instance 50° C., which is reached only after the vent phase has been concluded. The switch-back point of the snap-disc 26 lies in the drying phase before reaching the vent phase. If the pressure now increases in the vent phase, the chamber 26 can no longer be vented so that the lid 14 closes at the predetermined place X during the venting phase and the higher outside pressure subsequently holds the lid and thus the cap closed, since a residual vacuum prevails within the sterilization container. This vacuum is retained also when, at 50° C., the snap-disc 24 is moved back into the state known in FIGS. 1 and 6, as a result of which the arrangement automatically returns by itself into the basic position.

It is also possible to arrange the pressure-controlled or temperature-controlled release valve mechanism completely outside the sterilization container so that immediately after removal of a sealed container from the sterilizer, after the assumption of the basic position of the control, the latter can be used on another container.

In this connection, it is possible in various ways to convert the axial movement of the valve arrangement of the invention into an unlocking movement in a horizontal or any desired direction.

Figure 7:
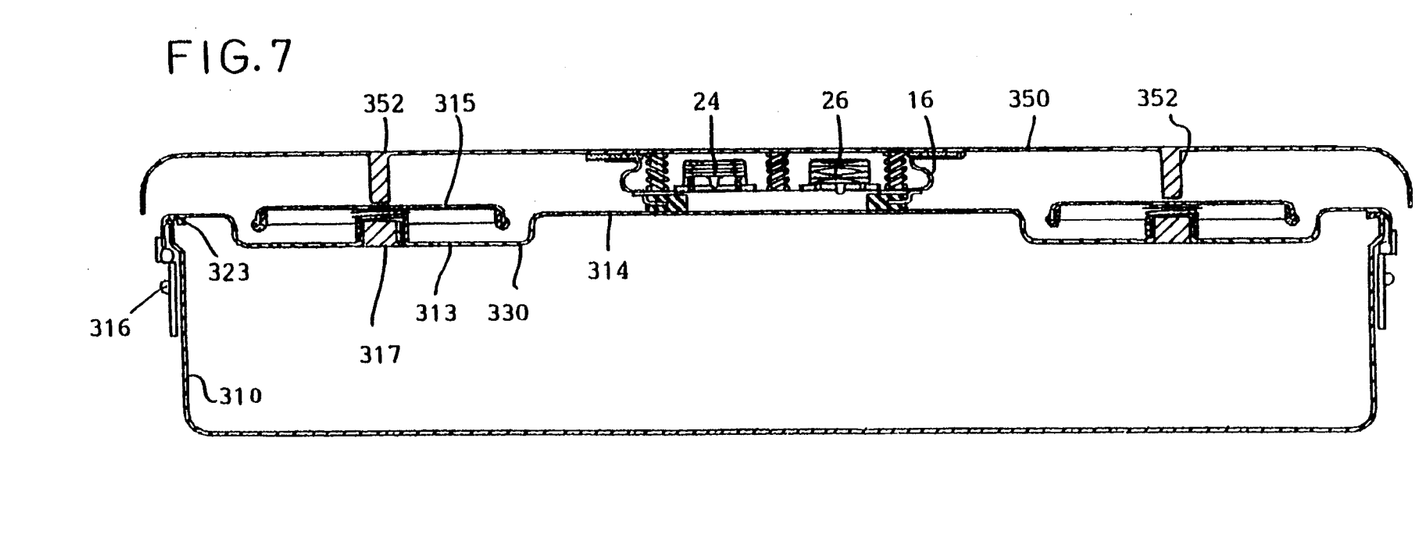
FIG. 7 shows another embodiment of a container with a removable release device provided with the valve arrangement.
Figure 8:
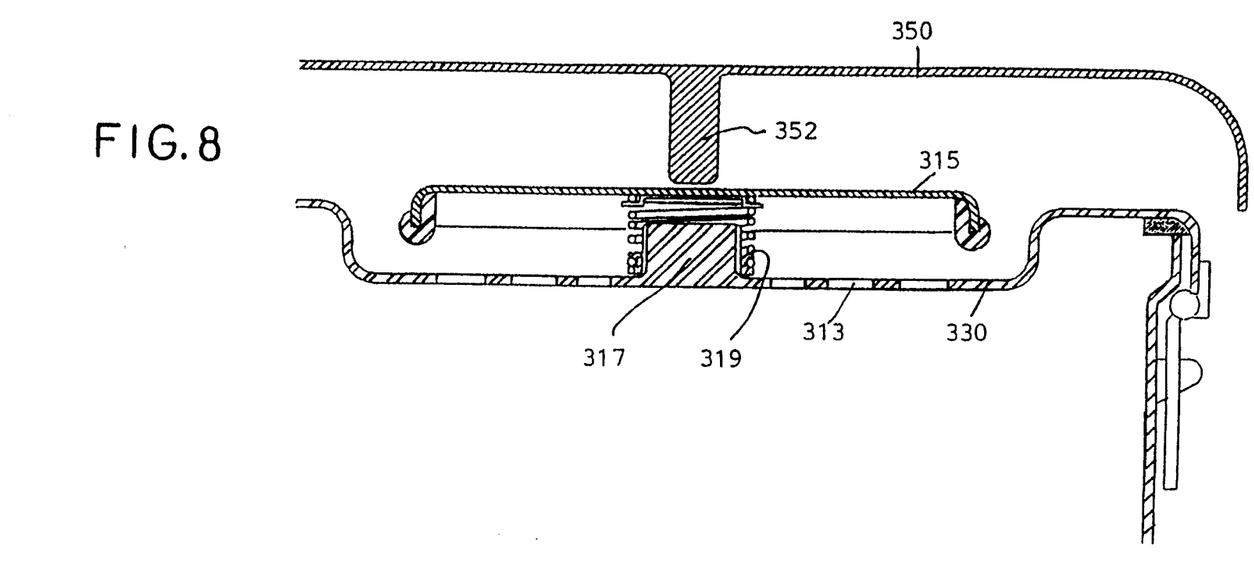
FIG. 8 shows, on a larger scale, a partial view of a container-lid closure according to FIG. 7.

FIGS. 7 to 9 show another embodiment in which the valve arrangement is removable from the sterilization container and can be used again. In this case, a container lid 314 can be clamped via container closures 316 on the container lower part 310, a sealing ring 323 producing a hermetic seal between lower part and lid. The lid 314 is provided with circular inwardly extending recesses 330 within which pressure equalization openings 313 are arranged. In the center of each recess 330, a guide pin 317 extends upward, a compressed coil spring 319 being placed on pin 317. The spring 319 firmly bears against a valve cap 315 on the upper end protruding above the pin. The valve cap 315 is provided at its edge with a circumferential seal and in a downward pressed condition seals off the depression 330 on the lid and thus, closes the pressure equalization openings 313.

For the control of the valve caps 315, a switch device is employed which has a lid 350 having on its inner side the valve arrangement of the snap-disc valves 24, 26 according to FIG. 1. The valves are surrounded by a bellows 16, the base plate 360 of which has an angularly bent linearly extending flange 362 on two opposite sides which are pushed laterally into the groove of two holding ledges 364 applied on the container lid 314 and thus produce in the vertical direction a form-locked connection between the container lid 314 and the lid 350. The lid 350 is provided with downwardly pointing switch pins 352 which are aligned in an inserted state with the guide pins 317 and rest on the valve caps 315.

The device shown in FIGS. 7 to 9 operates as follows:

For sterilization, lid 350 bearing the valve arrangement has its flanges 362 inserted into the grooves of the holding ledges 364 of container lid 314. The lid 314 itself is placed on the lower container part 310 in a sealing manner, via the clamping closures 316 and the seal 323. During the sterilization process, the valve arrangement surrounded by the bellows 16 operates in the same manner as described in connection with the embodiment according to FIG. 1. In other words, during the vent phase the bellows 16 collapses axially due to the pressure difference prevailing, as a result of which the lid 315 is pressed against the container lid 314. In this way, the switch pins 352 press the valve caps 315 downward against the action of the springs 319, as a result of which the pressure equalization openings 313 are closed. The sterilization container is now hermetically sealed from the outside. This switching process takes place in the vent phase before reaching the surrounding pressure, so that a vacuum remains within the container and keeps the valve cap 315 closed even when the lid 315 is laterally removed. The condition of closure of the valve caps can be clearly visually noted from the outside. If, due to a leak, pressure equalization takes place between the inside pressure and outside pressure, the valve caps 350 are lifted off by the springs 319 and these lifted valve caps constitute a clear indication that the container has lost its vacuum and is no longer tightly closed. In this way, there is a clear indication of a leak.

The sterilization container of FIGS. 10–13 has a container lower part 110, a lid 112 and an intermediate lid 114 and, between these lids, there is a valve arrangement 116 which has been described in connection with FIGS. 1 and 9.

Figure 13:
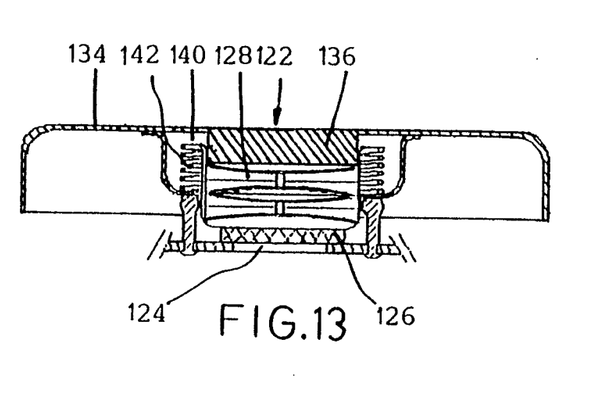
FIG. 13 shows, on a larger scale, the closed condensate discharge valve of FIG. 12.

The container lower part 110 has a bottom 118 which descends towards the center and is supported by a base 120. Above the lowest point of the bottom 118, there is arranged a condensate discharge valve 122. The construction and manner of operation of condensate discharge valve 122 can be noted most clearly from FIGS. 11 and 13. Above a condensate discharge opening 124 at the lowest point of the bottom 118, there is a valve disc 126 which, in a closed position as shown in FIG. 13, seals off the opening 124. The valve disc 126 is fastened on the bottom of a beaker 130 which receives a package of snap- discs 128 which effects the temperature-dependent valve control. For the purpose of the control of the condensate discharge valve, the upper switch temperature of the snap-discs is preferably set to about 130° C. and the lower switch-back temperature preferably to about 110° C. Within the snap-disc package, the individual snap-discs are preferably assembled with the concave surfaces facing in opposite directions.

Within the container bottom a support ring 132, provided with an internal thread, is fastened around the outlet opening 124. The ring 132 has, adjacent the bottom 118, openings (not shown in the drawing) for the flow of the condensate. This support ring supports a rigid sleeve 138 which is threaded into the ring 132, or over it, or can be fixed in some other manner. This rigid sleeve 138 is fastened by an outwardly bent flange to the bottom of a cover cap 134, which is so arranged for the protection of the condensate discharge valve that a narrow outlet slot 133 of a few millimeters still remains between the lower edge of the cap and the bottom 118 of the container. This cover cap remains continuously in the position shown in FIGS. 10 and 12.

On its inner side, the cover cap 134 bears a guide plug 136 which extends into the beaker 130, along which plug the beaker slides during the switching process. The beaker has an outwardly pointing flange 140, against the bottom of which there rests a compression coil spring 142 which surrounds the beaker and the lower end of which rests against the support ring 132 or the spacer bolts.

Figure 10:
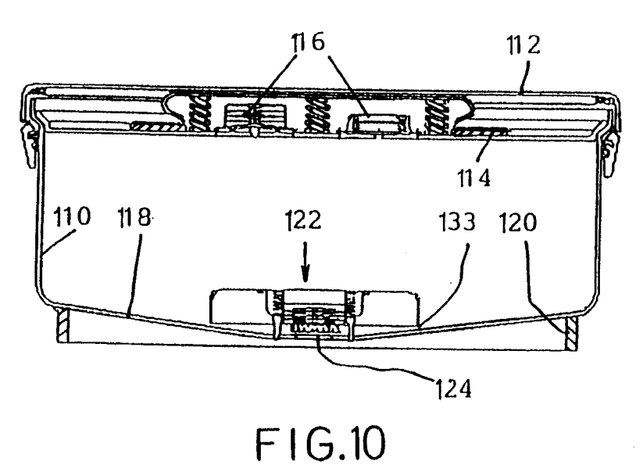
FIG. 10 is a vertical cross-section through a sterilization container with a condensate discharge valve developed in accordance with the invention, the valve being in open position.
Figure 11:
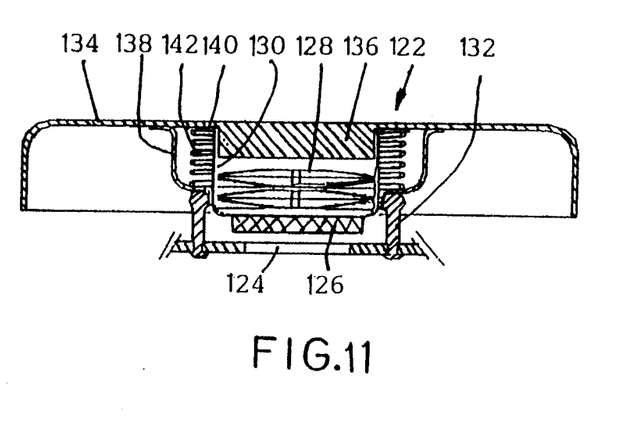
FIG. 11 shows, on a larger scale, the condensate discharge valve of FIG. 10 in the open position.
Figure 12:
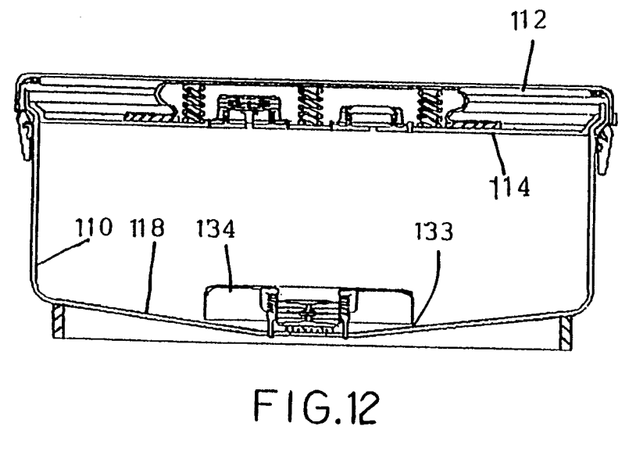
FIG. 12 is a view corresponding to FIG. 10, of a sterilization container with the condensate discharge valve being closed.

The condensate outlet valve shown in FIGS. 11 and 13 can cooperate directly with discharge opening 124 in the container bottom 118, as shown in FIGS. 10 and 12. However, the condensate outlet valve can also be used to open or close the inlet opening of a separate condensate collection container which can be inserted into the sterilization container, as shown in FIGS. 14 and 15.

Figure 14:
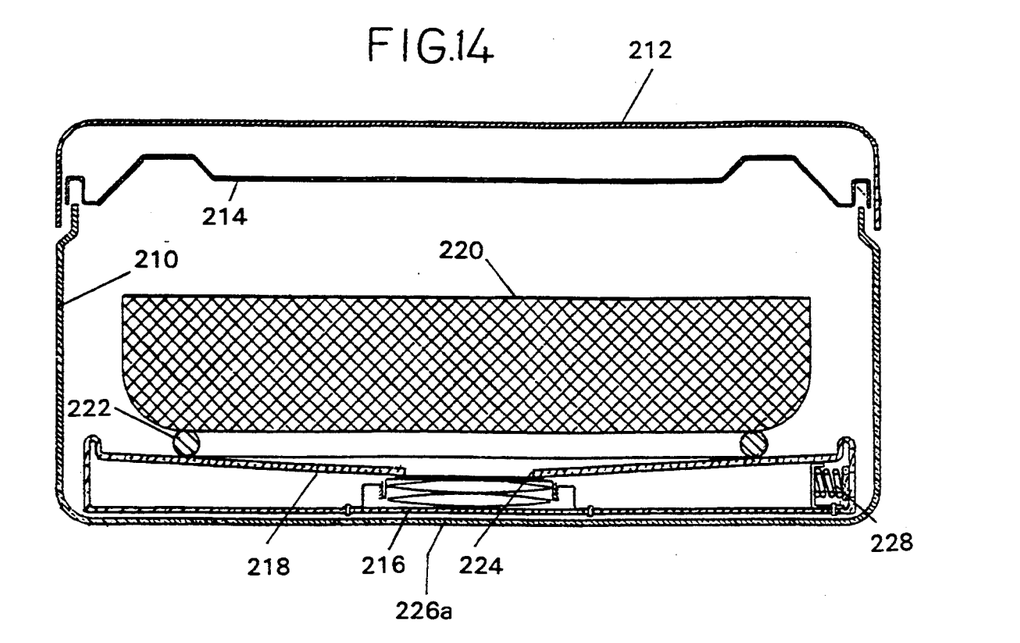
FIG. 14 is a cross-sectional view of a sterilization container with a loosely inserted condensate collection container, the inlet valve of which is temperature-controlled.
Figure 15:
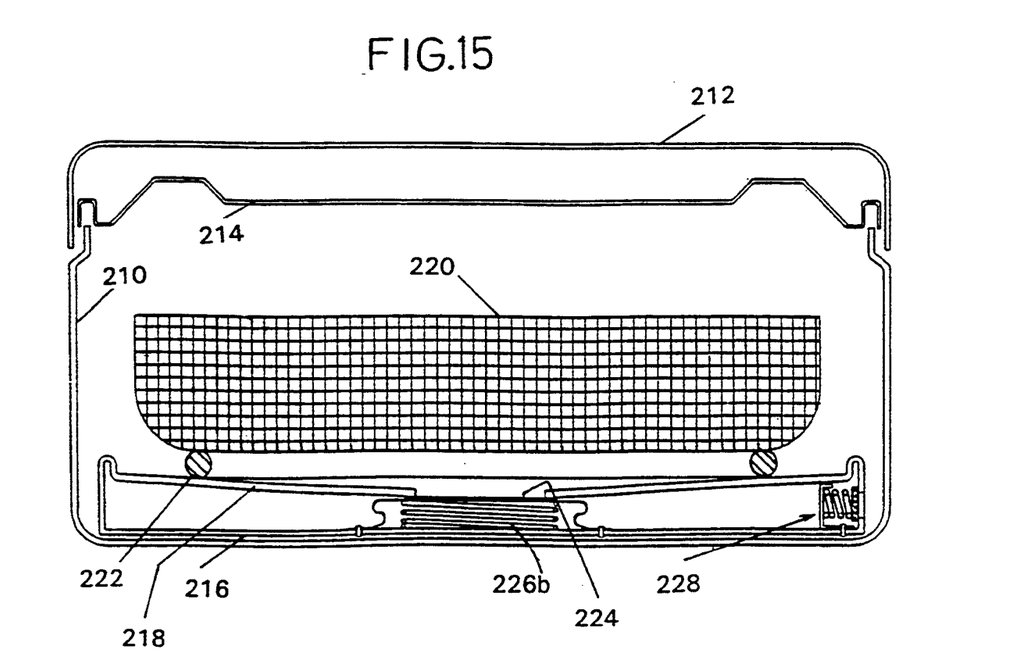
FIG. 15 is a cross-sectional view of a sterilization container having a condensate collection container, the inlet valve of which is pressure-controlled.

The sterilizer container shown in FIGS. 14 and 15 consists of container lower part 210, container lid 212 and an intermediate lid 214, which has either filters or valves for the exchange of flow in the sterilization.

Within the container lower part 210, there is arranged a flat condensate collection container 216 which extends substantially over the entire bottom surface of the sterilizer container and has a slightly conically developed funnel-shaped top 218 which serves as a standing surface for the standing rim 222 of an instrument basket 220. At the lowermost point of the top side 218 of the collection container, there is a discharge opening 224 which can be closed by a valve 226a. As shown in FIG. 14, the valve 226a is developed as a temperature-controlled valve, for instance in the manner shown in FIGS. 11, 13, i.e. the valve is opened at the temperatures prevailing in the sterilization phase and passes into the closed condition, shown in the drawing, as soon as the temperature within the sterilizer drops below a predetermined value.

Preferably, but not necessarily, this switch temperature is above the boiling point of water at normal pressure, so as to be able to close the collection container as early as possible upon a drop in pressure, and thus of temperature, and thus to be able to "enclose" as much condensate as possible. In principle, however, every switch temperature which lies above the temperature reached during the drying vacuum holds back from evaporation a variable partial quantity of the condensate originally enclosed in the collection container, while the other part is evaporated during the closing process of the collection container. The variable partial quantity increases the closer the closing temperature gets to the sterilization temperature, the optimal adjustment thereof being expressly reserved.

In the embodiment shown in FIG. 15, the valve 226b includes a pressure-controlled spring, i.e., it opens and remains open from a given pressure during the pressure phases of the sterilization program and closes the collection container in a gas-tight manner when this pressure is dropped below the given values.

If the condensate collected is not in any event discharged after the use of the collection container and before its next use, simply by manual actuation of the inlet valve 226a, 226b, an additional condensate discharge valve 228 can, in order to facilitate the handling, be arranged for instance on the narrow edge of the collection container.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

I claim:
1. A sterilization system comprising:
   a sterilizer means having a sterilization cycle, the cycle having a sterilization phase, a drying phase following the sterilization phase, and a venting phase following the drying phase;
   a sterilization container having a pressure chamber therein, said container being configured to be placed within said sterilizer means;
   first valve means located within aid pressure chamber of said sterilization container, the first valve means being moveable between an open position wherein an exchange of fluid between the container and the sterilizer means takes place during the sterilization phase, and a closed position where said first valve means closes a first venting opening in said pressure chamber;
   second valve means located in said pressure chamber for movement between a closed position wherein said second valve means closes a second venting opening in said pressure chamber and an open position wherein pressure equalization of said pressure chamber occurs;
   a first temperature sensor disposed in said first valve means which enables said first valve means to close said first vent opening at a first predetermined temperature, the sterilizer means reaching said first predetermined temperature during the sterilization phase;
   a second temperature sensor disposed in said second valve means for enabling said second valve means to open said second vent opening and for reclosing said second vent opening when the sterilizer means reaches a second predetermined temperature during the drying phase, wherein when said first and second vent openings are closed pressure equalization of said pressure chamber ceases;
   a bellows disposed between a normally open outer lid and an inner lid of the container, the inner lid having fluid exchange openings which permit the exchange of fluid between the container and the sterilizer means during the sterilization and drying phases, said bellows forming said pressure chamber, and said first and second valve means being disposed within said bellows.

2. A sterilization system according to claim 1, wherein said first and second temperature sensors each comprise at least one snap disc which is constructed and arranged to automatically switch over into an opposite state of curvature at a predetermined temperature and to automatically switch back to an original state of curvature determined by hysteresis and cooling.

3. A sterilization system according to claim 1, wherein said first temperature sensor enables said first valve means to reopen said first vent opening at a third predetermined temperature, said sterilizer means reaching said third predetermined temperature after the venting phase.

4. A sterilization system according to claim 1, further comprising springs disposed within said bellows for biasing the outer lid in an open position, wherein when the first and second vent openings are closed and pressure equalization of said pressure chamber ceases, external pressure in the sterilizer means compresses the springs forcing the outer lid to close.

5. A sterilization system according to claim 1, wherein said inner lid includes a plurality of spring biased valve caps disposed above the pressure equalization openings.

6. A sterilization system according to claim 5, wherein said outer lid includes a plurality of pins extending toward the valve caps, wherein when the first and second vent openings are closed and pressure equalization of said pressure chamber ceases, external pressure in the sterilizer means compresses the outer lid, the pins forcing the valve caps to close.

7. A sterilization system according to claim 1, wherein the bellows are fixed to the inner lid by a form-locked connection.

8. A sterilization system comprising:
a sterilizer means having a sterilization cycle, the cycle having a sterilization phase, a drying phase following the sterilization phase, and a venting phase following the drying phase;
a sterilization container having a pressure chamber therein, said container being configured to be placed within said sterilizer means;
first valve means located within said pressure chamber of said sterilization container, the first valve means being moveable between an open position wherein an exchange of fluid between the container and the sterilizer means takes place during the sterilization phase, and a closed position where said first valve means closes a first venting opening in said pressure chamber;
second valve means located in said pressure chamber for movement between a closed position wherein said second valve means closes a second venting opening in said pressure chamber and an open position wherein pressure equalization of said pressure chamber occurs;
a first temperature sensor disposed in said first valve means which enables said first valve means to close said first vent opening at a first predetermined temperature, the sterilizer means reaching said first predetermined temperature during the sterilization phase;
a second temperature sensor disposed in said second valve means for enabling said second valve means to open said second vent opening and for reclosing said second vent opening when the sterilizer means reaches a second predetermined temperature during the drying phase, wherein when said first and second vent openings are closed pressure equalization of said pressure chamber ceases;
a condensate discharge valve means for movement between an open position wherein condensate flows from an outlet opening in the bottom of the container and a closed position wherein the condensate discharge valve means seal the outlet opening; and
a third temperature sensor located within the condensate discharge valve means which enables the condensate discharge valve means to close the opening, said third temperature sensor being disposed within a beaker and bearing a valve disc for closing the outlet opening at a fourth predetermined temperature, the sterilizer means reaching the fourth predetermined temperature during the drying phase.

9. A sterilization system according to claim 8, wherein the third temperature sensor comprises a snap-disc which is constructed and arranged to automatically switch over into an opposite state of curvature at a predetermined temperature and to automatically switch back to an original state of curvature determined by hysteresis and cooling.

10. A sterilization system according to claim 8, further comprising a support ring fastened around the outlet opening, the beaker being axially movable within the support ring.

11. A sterilization system according to claim 10, further comprising a stationary cover connected to the support ring for protecting the condensate discharge valve means.

12. A sterilization system according to claim 10, further comprising biasing means disposed between the beaker and the support ring for biasing the valve disc in a normally open position.

* * * * *